US005393784A

United States Patent [19]
Richardson

[11] Patent Number: 5,393,784
[45] Date of Patent: Feb. 28, 1995

[54] TREATMENT OF TARDIVE DYSKINESIA WITH LEUCINE, ISOLEUCINE, VALINE OR MIXTURES THEREOF

[75] Inventor: Mary Ann Richardson, New York, N.Y.

[73] Assignee: New York State Office of Mental Health, Albany, N.Y.

[21] Appl. No.: 93,955

[22] Filed: Jul. 21, 1993

[51] Int. Cl.⁶ ............................................. A61K 31/195
[52] U.S. Cl. ................................................... 514/561
[58] Field of Search ........................................... 514/561

[56] References Cited

U.S. PATENT DOCUMENTS

| | | | |
|---|---|---|---|
| 4,129,652 | 12/1978 | Faxe | 424/247 |
| 4,138,484 | 2/1979 | Faxe | 424/247 |
| 4,209,531 | 6/1980 | Berry | 424/319 |
| 4,252,822 | 2/1981 | Berry | 424/319 |
| 5,028,622 | 7/1991 | Plaitakis | 514/561 |

OTHER PUBLICATIONS

Richardson, et al., "The prevalence of tardive dyskinesia in a mentally retarded population," *Psychopharmacol. Bull.*, 22:243–249, 1986.
Scriver, C. R., et al., "The hyperphenylalaninemias," *The Metabolic Basis of Inherited Disease*, edited by Scriver, et al, D. New York, N.Y., McGraw Hill, 1989, pp. 495–546.
*Psychopharmacol. Bull.* 25:47–51 (1989); "Amino acid metabolism and tardive dyskinesia vulnerability in schizophrenia".
"Preliminary Support for the Oral Administration of Valine, Isoleucine and Leucine for Phenylketouria," *Developmental Medicine and Child Neurology*, 27:33–39 (1985).
"Reduction of Cerebral Spinal Fluid Phenylalanine after Oral Administration of Valine, Isoleucine, and Leucine," *Pediatric Research*, 16:751–755 (1982).
Adibi, et al., "Branched Chain Amino and Keto Acids in Health and Disease," *Basil:Karger* (1984).
Van Woert, et al., *Monographs in Neural Sciences*, 3, 71–80, (1976).
Avanzini, et al., *Monographs in Neural Sciences*, 5, 142–152 (1980).
Jacobs, et al., *Gilles de la Tourette Syndrome*, eds. Friedhoff, A. J. and Chase, T. N., pp. 93–97, New York: Raven Press (1982).
Sandyk, R., et al., "L-tryptophan in drug-induced movement disorders with insomnia," *N. Engl. J. Med.* 1986, 314(19):1257.
Sandyk, R, et al., "L-tryptophan in neuroleptic-induced dyskinesia," *Int. J. Neurosci.*, 1988, 42:127–130.
Nasrallah, H. A., et al. "Serotonin precursor effects in tardive dyskinesia," *Pharmacology*, 1982, 77:234–235.
Jus, K., et al. "Studies on the action of certain pharmacological agents on tardive dyskinesia and on the rabbit syndrome," *Int. J. Clin. Pharmacol.* 1974, 9(2):138–145.
Lakke & Teelken, *Neurology*, 26, 489–493 (1976).
Seeman, P., *J. Clinical Psychopharmacol.*, 8 (4, supp):3S–9S (1988).
Jeste, et al., *Br. J. Psychiatry*, 144:177–180 (1984).
Wagner, et al., *J. Clinical Psychopharmacol.*, 2:312–314 (1982).
Kaufman, et al., *Biol. Psychiatry*, 21:799–812 (1986).
Tamminga, et al., *Arch. Gen. Psychiatry*, 36:595–598 (1979).
Thaker, et al., *Arch. Gen. Psychiatry*, 44:522–529 (1987).
Stahl, et al., *Biol. Psychiatry*, 20:888–893 (1985).
Andersson, et al., *Mov. Disord.*, 4(1):37–46 (1989).
Thaker, et al., *Biol. Psychiatry*, 25:49–59 (1989).
Gunne, et al., *Nature*, 309:347–349 (1984).
Lohr, et al., *Schizophr. Bull.*, 14:291–296 (1988).

(List continued on next page.)

*Primary Examiner*—Marianne M. Cintins
*Assistant Examiner*—T. J. Criares
*Attorney, Agent, or Firm*—Sughrue, Mion, Zinn, Macpeak & Seas

[57] ABSTRACT

The present invention relates to a method of remitting or attenuating the symptoms of tardive dyskinesia which can be secondary to treatment of psychiatric disorders with antipsychotic drugs, by administering leucine, isoleucine, valine or mixtures thereof.

6 Claims, No Drawings

OTHER PUBLICATIONS

Cadet, et al., *Ann. N.Y. Acad. Sci.* 570:176–185 (1989).

Lu, et al., *Biol. Psychiatry*, 25:717–724 (1989).

Pardridge, W. M., *Nutrition and the Brain*, vol. 7: 199–241, New York: Raven Press (1986).

Giovannini, M., et al., "Serotonin and noradrenaline concentrations and serotonin uptake in platelets from hyperphenylalanemic patients," *J. Inherited Metab. Dis.* 1988, 11:285–290.

Bjerkenstedt, L., et al., "Plasma amino acids in relation to cerebrospinal fluid membrane metabolites in schizophrenic patients and healthy controls," *Br. J. Psychiatry*, 1985, 147:276–282.

Delgado, P. L., et al., "Serotonin function and the mechanism of antidepressant action. Reversal of antidepressant-induced remission by rapid depletion of plasma tryptophan," *Arch. Gen. Psychiatry*, 1990, 47:411–418.

Sloviter, R. S., et al., "Serotonergic properties of b–phenylethylamine in rats," *Neuropharmacology*, 1980, 19:1071–1074.

Dourish, C. T., "Behavioral effects of acute and chronic b-phenylethylamine administration in the rat: evidence of the involvement of 5-hydroxytryptamine," *Neuropharmacology*, 1981, 20:1067–1072.

Hagenfeldt, L., et al., "Amino acids in plasma and CSF and monoamine metabolites in CSG: interrelationship in healthy subjects," *J. Neurochem.*, 42(3):833–837, 1984.

Rao, J. L., et al., "Serum amino acids, central monoamines, and hormones in drug-naive, drug-free, and neuroleptic-treated schizophrenic patients and healthy subjects," *Psychiatry Res.*, 34:243–257, 1990.

Gardos, et al., "The Acute Effects of a Loading Dose of Phenylalanine in Unipolar Depressed Patients With and Without Tardive Dyskinesia," *Neuropsychopharmacology*, 1992, vol. 6, No. 4.

Richardson, et al., *Biological Psychiatry*, vol. 2, "Proceedings fo the 5th World Congress of Biological Psychiatry," (*Excerpta Medica*), 1991, pp. 341–343.

*2nd International Symposium on Serotonin from Cell Biology to Pharmacology and Therapeutics*, Sep., 1992, Abstract Book, p. 4.

*Joint Meeting of 4th International Trace Amines Conference and 5th International Amine Oxides Workshop, Aug., 1992.*

Bowers, et al., *J. Clinical Psychopharmacol.*, 7:57–58 (1987).

Fibiger, et al., *TINS*, pp. 462–464 (Dec. 1984).

Stegink, L. D., et al., *Aspartame Physiology and Biochemistry*, New York: Marcel Dekker, pp. 509–553 (1984).

Bremer, H. J., et al, *Disturbances of Amino Acid Metabolism: Clinical Chemistry and Diagnosis*, Baltimore: Urban & Schwarzenberg, 1981.

Bowers et al, *J. Clin Psychopharmacol*, vol. 7, No. 1, Feb. 1987 pp. 57–58.

Richardson, et al., *Journal of Psychopharmacology*, 7(2) (1993) pp. 219–220.

TREATMENT OF TARDIVE DYSKINESIA WITH LEUCINE, ISOLEUCINE, VALINE OR MIXTURES THEREOF

FIELD OF THE INVENTION

The present invention relates to the treatment of abnormal movement disorders through the manipulation of the amino acids in the blood plasma pool.

BACKGROUND OF THE INVENTION

Neuroleptic drugs, including haloperidol, thioridazine, chlorpromazine, flupenazine and thiothixene, are used as antipsychotics to treat a number of psychoses, such as schizophrenia, schizoaffective disorder, organic psychosis, bipolar disorder, and unipolar depression (severe form). This represents a sizable portion of Americans, as the National Institute of Mental Health reports that the number of patients in the United States with schizophrenia in 1990 was 1.8 million; bi-polar disorder, 1.1 million and unipolar depressives (severe form), 1.7 million. Neuroleptics are also used as behavioral control measures in the following non-psychotic populations; children with autism, child and adolescent psychiatric patients with conduct and adjustment disorders, the mentally retarded, and geriatric patients in general hospitals and nursing homes. In these populations, clinical trials have established that these agents are effective in the treatment of symptoms such as; tension, hyperactivity, combativeness, hostility, negativism, hallucinations, acute delusions, poor self-care, and sometimes withdrawal and seclusiveness. Neuroleptics are also the drug of choice to treat the symptoms of abnormal movements in primary neurological disorders; such as for patients with tic disorders (transient tic disorders, chronic motor tics, Tourettes' disorder) and those with Huntington's Disorder.

Unfortunately, in a large number of individuals, a variety of movement disorders may develop secondary to chronic neuroleptic treatment thereby creating a therapeutic dilemma in the mental health community. Among these disorders are tardive dyskinesia (TD), Parkinsonism, tardive dystonia, akathisia and neuroleptic malignant syndrome.

A similar class of drugs, as represented by the drug methochlorpromide, used as anti-vomiting agents (particularly for cancer chemotherapy patients) are also known to cause a similar set of movement disorders. Additionally, a variety of movement disorders are seen secondary to other drugs such as lithium (used for the treatment of bipolar disorder), anticonvulsants (used for the treatment of seizure disorders), benzodiazepines (used for the treatment of anxiety disorders), and tricyclic antidepressants (used for the treatment of unipolar depression).

Abnormal movements are also seen as primary neurological disorders. In addition to the two such conditions mentioned above, tic disorders and Huntington's Disorder, there are many other neurological disorders that are manifested by abnormal movements; these include, myoclonic syndromes, childhood and adult onset dystonias, Wilson's disease, Sydenham's chorea, and other choreas. Several dementias also manifest an abnormal movement component; these include, Alzheimer's disease, Creutzfeldt-Jakob disease, Pick's Disease and Hallervorden Spatz Disease.

The present invention relates to the treatment of abnormal movement disorders, including those mentioned in the sections above, whether they are secondary to drug treatment or primary disorders.

These abnormal movement disorders result in a wide variety of symptoms which can range from unconscious movements which interfere very little with quality of life, to quite severe and disabling movements. Examples of symptoms which are seen secondary to neuroleptic treatment are; involuntary tongue protrusions, snakelike tongue movements, repetitive toe and finger movements, tremors of extremities or whole body sections, muscular rigidity, slowness of movement, facial spasms, acute contractions of various muscles, particularly of the neck and shoulder which may eventually lead to painful, prolonged muscle contraction, restlessness, distress and an inability to remain still.

Thus, while patients suffering from psychoses such as schizophrenia need treatment with neuroleptics to control their psychoses, it can be difficult to integrate these patients back into the mainstream because the movement disorder side effects of their neuroleptic treatment produce a visual stigma, a stigma which is a barrier to complete acceptance of these patients in the world beyond a hospital or a halfway house.

Consequently, even though neuroleptic treatment may offer the best means of effectively treating patients who suffer from various psychoses, a pervasive fear that one or more of these abnormal movement disorders will develop and persist exists among psychiatric patients, their families and their psychiatrists. This fear results in a psychological cap on the therapeutic potential of these neuroleptic drugs to treat psychosis. It should be noted that the development of TD has been the cause of malpractice suits brought against psychiatrists.

One means of removing this barrier to continued and necessary treatment with neuroleptics has been the development of atypical neuroleptic drugs (one of which, clozapine, is available in the U.S.). These drugs are less likely to result in movement disorder side-effects. However, clozapine has some disadvantages relevant to our concerns; it was developed too late to help some patients, carries the risk of other serious life-threatening side effects which require expensive monitoring, and thus is not appropriate to all. For instance, some public mental health facilities, because of cost issues, must necessarily limit the use of this drug to only a small segment of the population that they treat.

The present inventor has conducted a 15 year course of study in neuroleptic-induced abnormal movement disorders. This work is represented by the work she has done to define the etiology, pathophysiology, and to develop treatment and preventive strategies for one of the neuroleptic-induced movement disorders, TD. The research strategy in this facet of her work was to define risk factors for the development of this disorder in all the major neuroleptic treated populations (adult psychiatric patients, geriatric psychiatric patients, child psychiatric patients and the mentally retarded), to search for commonalities in these risk factors across populations and then to integrate these findings into a unitary biochemical paradigm for the pathophysiology of TD. The unitary paradigm that was generated from the data of these studies defines the metabolism of the large neutral amino acid, phenylalanine, as a pathophysiologic element in TD. The individual study findings that most directly led to this paradigm were those of a large scale point prevalence study of TD among mentally retarded (not psychotic) residents (n=211) of a state developmental center (Study one-see below). In that study the inherited metabolic disorder phenylketonuria (PKU) was found to be a strong and statistically significant risk factor for TD development. The power of that risk factor was demonstrated by the fact that eighty-six percent of the phenylketonurics in the sample had TD as compared to a rate of only 27% of the non-PKU population. This study is seminal in the field of neuroleptic-induced movement disorder research in that it was the first reported association of a medical condition (metabolic neurological disorder) with TD and thus provided a new direction for further research. That direction was the search in the well characterized pathophysiology of PKU for a clue to the pathophysiology of TD. It is well known that PKU is an inherited metabolic disease (carried on chromosome 12) in which the activity of phenylalanine hydroxylase, the enzyme responsible for conversion of the large neutral amino acid phenylalanine to tyrosine, is absent or drastically reduced. This deficit creates a condition in which there is a chronic excess of phenylalanine in the plasma and thus in the brain of PKU patients (Richardson, et al , "The prevalence of tardive dyskinesia in a mentally retarded population," *Psychopharmacol. Bull.*, 22:243-249, 1986; Scriver, C. R., Kaufman, S. and Woo, S. L. C., "The hyperphenylalaninemias," *The Metabolic Basis of Inherited Disease*, edited by Scriver, C. R., Beaudet, A. L., Sly, W. S. and Valle, D. New York, N.Y., McGraw Hill, 1989, pp. 495-546).

Given this clue and in the search for a unitary hypothesis across populations, the present inventor undertook a study to test whether the metabolic response of phenylalanine metabolism to a dietary challenge (protein load) differentiated male schizophrenic patients (the heaviest users of neuroleptics) with TD from those without the disorder and further, whether the metabolic response of the TD patients could be characterized as PKU-like (Study Two—see below). This means whether schizophrenic patients with TD would show significantly higher levels of phenylalanine after the challenge. This was in fact the case with the finding of significantly higher post challenge levels of phenylalanine and the phenylalanine/large neutral amino acid ratio (LNAA) or a PKU-like response in patients with TD (Richardson, et al., "The plasma phenylalanine/large neutral amino acid ratio: a risk factor for tardive dyskinesia," *psychopharmacol. Bull.* 25:47-51 (1989); "Amino acid metabolism and tardive dyskinesia vulnerability in schizophrenia", *Biological Psychiatry*, 2, 341-343 (*Excerpta medica*, 1991).

A large scale replication (Study Three; n=209 males; n=103 females) of Study Two found that the metabolic response to a phenylalanine challenge (100 mg/kg) dramatically and significantly distinguished males with TD from those without the disorder, thus establishing phenylalanine metabolism as a pathophysiological element in TD.

Berry, et al. (U.S. Pat. Nos. 4,252,822 and 4,209,531, and "PRELIMINARY SUPPORT FOR THE ORAL ADMINISTRATION OF VALINE, ISOLEUCINE AND LEUCINE FOR PHENYLKETOURIA," *Developmental Medicine and child Neurology*, 27:33-39 (1985) and "REDUCTION OF CEREBRAL SPINAL FLUID PHENYLALANINE AFTER ORAL ADMINISTRATION OF VALINE, ISOLEUCINE, AND LEUCINE," *Pediatric Research*, 16:751-755 (1982)) sought specifically to treat the behavioral, perceptual and cognitive symptoms of PKU with the branched chain large neutral amino acids, specifically isoleucine, leucine and valine (BCAA). The behavioral symptoms, some of which are motor in nature, are those of hyperactivity, irritability, poor impulse control, distractibility, aggressivity, and the stereotypical behaviors that are commonly seen in the mentally retarded such as rocking, jumping, running, spinning, flaying, etc. These investigators found that these agents (BCAA) were in fact effective in ameliorating many of the behavioral and cognitive target deficits and with a wider safety margin than with the routine treatment which consisted solely of a diet low in phenylalanine. In two separate studies, Berry, et al., literature supra. administered BCAA to PKU patients; in the first (two cases) they found that the cerebrospinal fluid serum ratio of phenylalanine was reduced and was accompanied by improvements in cognitive function (i.e., motor coordination and task learning). Cognitive improvement was also noted in the second study in three patients who had been treated with a phenylalanine restricted diet as infants and who had nearly normal IQs. The authors specifically found improvements in abstract reasoning and tactile-motor problems and coordination, thereby confirming that these cognitive tasks are particularly sensitive to the biochemical status of PKU patients. Although the behavioral problems improved by Berry, et al. can involve exaggerated movement, such as running, jumping and flaying movements; these are sharply distinguished medically from the abnormal movement disorders, primarily considered to be basal ganglia disease, which are the objectives to be treated herein. Prior to the present inventor's research, the role of phenylalanine in abnormal movement disorders seen secondary to neuroleptic treatment, such as TD, was unknown.

In addition to the work in PKU by Berry, et al., the BCAA as inhibitors of the uptake of aromatic amino acids at the blood-brain barrier neutral amino acid transport system, are used as therapy for several other neurological conditions Adibi, et al , "Branched Chain Amino and Keto Acids in Health and Disease," *Basil:Karger* (1984).

In one of these, hepatic encephalopathy, BCAA treatment is used successfully to decrease brain transport of the aromatic amino acids (phenylalanine, tyrosine and tryptophan) and of methionine. Two other disorders, maple syrup urine disease and isovaleric acidemia, whose pathology involves inability to catabolize the BCAA and thus cause excess levels of plasma BCAA, are treated by dietary alteration of plasma BCAA levels. Symptoms of maple syrup urine disease are neurological and include movement disorders (i.e., rigidity) and severe mental retardation. Therapy with a diet low in BCAA has been effective only if started immediately after birth.

In addition to the therapeutic use of the branched chain large neutral amino acids in the disorders mentioned above, the aromatic large neutral amino acid, tryptophan has been shown to impact in a complex manner on the symptoms of abnormal movement disorders. For instance, for the myoclonic syndromes and Tourette's disorder there are reports that both augmenting and depressing tryptophan supply to the brain can reduce symptoms (Van Woert, et al., *Monographs in Neural Sciences*, 3, 71-80, (1976); Avanzini, et al., *Monographs in Neural Sciences*, 5, 142-152 (1980); Jacobs, et al., *Gilles de la Tourette Syndrome*, eds. Friedhoff, A. J. and Chase, T. N., pp. 93-97, New York: Raven Press (1982)). This complexity and a further lack of replication has also been seen in the use of tryptophan for the modulation of TD symptoms. Two case reports showed a reduction of TD symptoms following administration of L-Tryptophan to a patient who was receiving the agent for insomnia; the finding was repeated in a second patient also being treated for insomnia (Sandyk, R., Consroe, P. F., Iacono, R. P., "L-tryptophan in drug-induced movement disorders with insomnia," *N. Engl. J. Med.* 1986, 314(19):1257; Sandyk, R., Bamford, C. R., Khan, I. Fisher, H., "L-tryptophan in neuroleptic-induced tardive dyskinesia," *Int. J. Neurosci.*, 1988, 42:127–130). However, earlier work with seven patients reported no change in TD with concomitant administration of 5-hydroxytryptophan and carbidopa (Nasrallah, H. A., Smith, R. E., Dunner, F. J., McCalley-Whitters, M., "Serotonin precursor effects in tardive dyskinesia," *Pharmacology*, 1982, 77:234–235) or in 4 patients with the administration of D-L tryptophan (Jus, K., Jus A., Gautier, J. Villeneuve, A. Pires, P. Pineau, R., Villeneuve, R., "Studies on the action of certain pharmacological agents on tardive dyskinesia and on the rabbit syndrome," *Int. J. Clin. Pharmacol.* 1974, 9(2):138–145).

SUMMARY OF THE INVENTION

Accordingly, an object of the present invention is to provide a method of treating abnormal movement disorders.

A more specific object of the present invention is to provide a method of treating abnormal movement disorders which arise secondary to drug administration, especially secondary to treatment with neuroleptics.

Another more specific object of this invention is to provide a method of treating abnormal movement disorders which manifest themselves as part of a primary neurological disorder or disease, primarily those of basal ganglia disease.

Another object of this invention is to provide a method of treating tardive dyskinesia (TD), Parkinsonism, tardive dystonia and akathisia.

Another object of the present invention is to provide a method of treating tardive dyskinesia secondary to neuroleptic treatment.

These and other objects of the present invention have been met by a method which includes administration to the patient of large neutral amino acids in order to manipulate the amino acid profile of the blood plasma pool.

In certain preferred embodiments of the present invention, branched chain amino acids or aromatic amino acids are administered to alleviate (remit or reduce) the abnormal secondary movement disorders which arise as the result of treatment with a drug.

In a very preferred embodiment of the present invention, branched chain amino acids or aromatic amino acids are administered to alleviate movement disorders arising secondarily to treatment with neuroleptics.

In certain other preferred embodiments of this invention, branched chain amino acids or aromatic amino acids are administered to alleviate abnormal movement disorders seen as a symptom of a primary neurological disorder or disease.

In a very preferred embodiment of this invention, isoleucine, leucine and/or valine are administered to alleviate the symptoms of the movement disorder, TD.

In the present invention, all amino acids employed are L-, that is, the naturally occurring optical isomer configuration.

DETAILED DESCRIPTION OF THE INVENTION

TD is a drug-induced abnormal movement disorder that belongs to a broad category of movement disorders known as extrapyramidal movement disorders. This category generally involves pathology of a group of subcortical brain structures known collectively as the basal ganglia, as distinguished from other movement disorders caused primarily by disorders of the cerebral cortex, spinal cord, cerebellum, peripheral nerves or musculature, although in some conditions these other areas may be involved. In addition to TD, basal ganglia diseases include Parkinson's disease, drug-induced parkinsonism, the choreas, ballism, the athetoses, the dystonias including tardive dystonia, akathisia, Huntington's disease, several degenerative and atrophic syndromes, and several toxic and infectious processes.

How the basal ganglia control movements is poorly understood, but generally dysfunction may involve cellular loss, metabolic dysfunction or dysregulation of electrical-type input/output balance. Some of these defects may be compensated for by manipulation of neurotransmitter synthesis or release; one way this can be achieved is by dietary control of the supply of neurotransmitter precursor amino acids at the blood brain barrier as the blood brain barrier has transport systems that mediate the bi-directional flux of amino acids. The major neurotransmitter precursor amino acids enter the brain via the L-system (the L stands for "leucine") which transports neutral amino acids between blood and brain in a competitive manner.

In addition to the Richardson, et al. work showing that TD may involve relatively higher levels of the amino acid phenylalanine, this amino acid has been shown to be elevated in the cerebrospinal fluid of Parkinson's disease, senile dementia, dystonia musculorum deformans, chorea athetosis, and essential and hereditary tremor (Lakke & Teelken, *Neurology*, 26, 489–493 (1976)). Thus, amino acid transport defects involving phenylalanine may be common to a number of neurological disorders, and the action of a dietary supplement of large neutral amino acids can be seen as an effective, and efficient potential treatment across a broad range of neurological disorders.

The public health consequences of TD have driven researchers to the generation of a large body of research trying to unearth the pathophysiology of the disorder. These studies have led to diverse hypotheses which focus on dopaminergic (Bowers, et al., *J. Clinical Psychopharmacol.*, 7:57–58 (1987); and Seeman, P., *J. Clinical Psychopharmacol.*, 8 (4, supp):3S–9S (1988)), noradrenergic (Jeste, et al., *Br. J. Psychiatry*, 144:177–180 (1984); Wagner, et al., *J. Clinical Psychopharmacol.*, 2:312–314 (1982); and Kaufman, et al., *Biol. Psychiatry*, 21:799–812 (1986)), gabaergic (Tamminga, et al., *Arch. Gen. Psychiatry*, 36:595–598 (1979); Fibiger, et al., *TINS*, pp. 462–464 (December 1984); Thaker, et al., *Arch. Gen. Psychiatry*, 44:522–529 (1987); Stahl, et al., *Biol. Psychiatry*, 20:888–893 (1985); Andersson, et al., *Mov. Disord.*, 4(1):37–46 (1989); Thaker, et al., *Biol. Psychiatry*, 25:49–59 (1989); and Gunne, et al., *Nature*, 309:347–349 (1984)), or free radical mechanisms (Lohr, et al., *Schizophr. Bull.*, .14:291–296 (1988); and Cadet, et al., *Ann. N.Y. Acad. Sci.* 570:176–185 (1989)).

These above-mentioned proposed mechanisms have been evaluated based on measurements of the correlation of various biochemicals, such as dopamine, norepinephrine, serotonin, their respective metabolites and products of free radical peroxidation thereof, which are measured in the plasma, urine and cerebrospinal fluid of patients with symptoms of TD. However, most often, these correlations are inconsistent with clinical observations and the results of treatment trials based on the postulated mechanisms.

In one study of several neurochemical correlates of tardive dyskinesia, the researchers found no associations between the absolute levels of monoamine metabolites of these chemicals in cerebrospinal fluid, and the status of the patients' TD. However, this study did note significant reductions in the ratios of various neurotransmitter metabolites in the cerebrospinal fluid (Lu, et al., *Biol. Psychiatry*, 25:717-724 (1989)).

Overall, the previous work done in this area suggests that the manifestation of abnormal movement disorders such as TD, at minimum involve several neurotransmitter systems, and that vulnerability to such disorders, particularly upon treatment with neuroleptic drugs, may be multifactorial.

The present inventor has performed several studies relating to neuroleptic-induced movement disorders in her 15 years in the field. In both her research and in her clinical work directing a Clinical Movement Disorders Program for the New York State Office of Mental Health she has evaluated and recommended treatment for several hundred patients suffering from such disorders. As described in the Background section above, the prelude to the present invention were several large scale epidemiological studies across several populations which had been designed by the present inventor to uncover risk factors for TD that could be used to define a unitary pathophysiological etiology for the disorder. One of these studies, in the mentally retarded, in finding that patients with PKU when treated with neuroleptic drugs were at particular risk for TD led to a consideration of the role of the aromatic large neutral amino acid, phenylalanine in TD. This study (Study One) was the first in a series of four investigations that led most directly to the present invention since it is known that in PKU the primary and causative defect is that phenylalanine is in excess in plasma and brain. Schizophrenia being the diagnostic category of psychotic disorders for which neuroleptics are most heavily prescribed, the present inventor then in a second study (Study Two) tested whether plasma phenylalanine levels would differentiate 53 male schizophrenics with TD from those without the disorder. Since it is known that these patients were not phenylketonurics and any defects in phenylalanine metabolism would necessarily be subtle, a protein challenge was used in an attempt to separate out patients whose phenylalanine metabolism could be a TD risk factor. It was found that the metabolic response to a protein challenge significantly discriminated patients with TD from those without the disorder in that those with TD had statistically significantly higher levels of phenylalanine and a statistically significant higher phenylalanine/large neutral amino acid ratio after the challenge. This finding was independent of the age of the subject.

A third study (Study Three) was a large scale replication of Study Two with some improved technical methodology; most importantly, the switch from a protein challenge to a phenylalanine challenge and the weight standardization of the phenylalanine challenge (100 mg/kg). This investigation was conducted in 209 psychotic males and 103 psychotic females. It was found that the phenylalanine challenge produced an even greater separation of TD Yes and TD No groups than had occurred in Study Two with again the TD Yes patients having statistically significant higher levels of both plasma phenylalanine and the phenylalanine/large neutral amino acid ratio. This finding was independent of the age of the patient.

In this work (Study Two and Three) the plasma level tells us the actual level of phenylalanine in the blood and the phenylalanine/ large neutral amino acid ratio gives us a marker relative to the other large neutral amino acids. This ratio thus provides information on brain levels of phenylalanine, or more specifically, the penetrance past the blood brain barrier of phenylalanine. This is so because it is known that phenylalanine competes with the other large neutral amino acids, such as tyrosine, tryptophan, isoleucine, leucine and valine for entry into the brain across the blood brain barrier. Moreover, of these large neutral amino acids, phenylalanine has the highest affinity for the blood brain barrier (Pardridge, W. M., In: Wurtman, et al., eds., *Nutrition and the Brain*, Volume 7: 199-241, New York: Raven Press (1986)). As a result, higher plasma levels of phenylalanine will lead to correspondingly lower brain levels of the neurotransmitter precursors tyrosine and tryptophan thus leading to lower levels of the neurotransmitters, dopamine, norepinephrine and 5-hydroxytryptophan (serotonin). Higher levels of the metabolites of phenylalanine inhibit the activities of tyrosine hydroxylase, tryptophan hydroxylase, and dopa decarboxylase which also leads to lower levels of these neurotransmitters. The relatively lower levels of serotonin and dopamine due to the higher levels of plasma phenylalanine and the phenylalanine large neutral amino acid ratio are believed related to the present invention since serotonin, dopamine, and serotonin-dopamine interactions are known to be of critical importance in movement control.

As a result of the three studies discussed above, the present inventor hypothesized for the first time that the levels of phenylalanine accumulated in the plasma and tissues of psychiatric patients play a role in whether such a patient will develop abnormal movement disorders, such as tardive dyskinesia, secondary to treatment with neuroleptic drugs.

More specifically, the present inventor believes that patients with TD may be experiencing small, but regular relatively higher elevations in plasma phenylalanine. These higher levels may be sufficient to effect a decreased transport of the competing aromatic amino acids, tyrosine and particularly tryptophan, into the brain. She speculates that the substance of TD vulnerability may be these relatively higher levels of plasma phenylalanine which by interfering primarily with tryptophan transport, may create primarily a hyposerotonergic and secondarily a hypodominergic neurochemical substrate. One of her further speculations is that this hyposerotonergia may be particularly important resulting in a physiological supersensitivity which when aggravated by neuroleptic treatment, may lead to TD. The present inventor has interpreted some of the data in the literature which suggests a strong inverse relationship between plasma phenylalanine and brain serotonin to support this speculation. One such study shows reduced synthesis of serotonin in mild hyperphenylalaninemics who are under good metabolic control and who have normal development without neurological signs or EEG abnormalities (Giovannini, M., Valsasina, R., Longhi, T., Cesura, A. M., Galva, M. D., Riva, E., Bondiolotti, G. P., Picotti, G. B., "Serotonin and noradrenaline concentrations and serotonin uptake in platelets from hyperphenylalaninemic patients," *J. Inherited Metab. Dis.* 1988, 11:285-290). Further, increased cerebrospinal levels of phenylalanine are associated with decreased CSF levels of tryptophan and its metabolites in schizophrenics with no known defects in phenylalanine metabolism (Bjerkenstedt, L., Edman, G., Hagenfeldt, L., Sedvall, G Wiesel F. A., "Plasma amino acids in relation to cerebrospinal fluid monoamine metabolites in schizophrenic patients and healthy controls," *Br. J. Psychiatry,* 1985, 147:276–282).

Most proximal to the present invention, however, was an unexpected Study Two finding. Within two hours after the high protein challenge meal rich in branched chain amino acids, the TD symptoms of patients with chronic TD were either greatly attenuated or totally remitted in greater than 50% of the 42 patients with the disorder. The plasma amino acid data collected and analyzed at the very point of the TD symptom remission gave the present inventor a clue that it was the branched chain amino acid enriched meal that caused this remission, and further that the remission was due to a temporary relief of the imbalance in the serotonin-dopamine interactions contributed to by a depression of the transport of tryptophan into the brain. The following Example 1 presents some of the details of Study Two which allow for an understanding of these unexpected findings of TD symptom remission which are most relevant to the present patent application. The following Examples are provided, however, for illustrative purposes only, and are in no way intended to limit the scope of the present invention.

EXAMPLE 1

In this study, 53 male schizophrenics were enrolled. In the last few months of the investigation 17 female schizophrenics were also entered into the study in order to collect pilot data on females. The numbers of females were insufficient, however, to allow for statistical analysis.

The protocol employed is also described in the aforementioned Richardson, et al. publication in *Psychopharmacol. Bull.,* Vol 25, No. 1, 1989, p. 47; although the unexpected TD symptom remission data was not included in that paper nor is it yet to be published.

Blood samples were drawn from patients after an overnight fast and 2 hours after the ingestion of a protein challenge. This challenge was served in the form of a breakfast which consisted of orange juice, a cheese omelette, ham, a waffle and coffee. The breakdown of the meal was 74.0 g of protein, 89.3 g of fat, and 42.1 g of carbohydrates which was equal to 3.6 g of phenylalanine, 0.9 g of tryptophan, and 15.9 g of BCAA. The mean weight of a study patient was 75.4 kg; thus, the mean phenylalanine load per subject was about 50 mg/kg and the mean BCAA load was about 209 mg/kg (formulated of 57 mg/kg of isoleucine, 62 mg/kg of valine and 90 mg/kg of leucine).

The post-dietary challenge blood plasma samples were measured 2 hours after the challenge because data from a series of acute phenylalanine dosing studies showed that most of the subjects' showed peak phenylalanine plasma levels at a time point that is 2 hours after challenge administration (Stegink, L.D., In: Stegink, et al., eds., *Aspartame Physiology and Biochemistry,* New York: Marcel Dekker, pp. 509-553 (1983)).

For this same reason, TD was also rated at this 2 hour after challenge time point. Patients were again evaluated for their TD status at a time subsequent to the evaluation session.

The blood samples were assayed for the levels of plasma large neutral amino acids; phenylalanine, tyrosine, tryptophan, alanine, isoleucine, leucine, valine, histidine, and threonine, and for the levels of phenylethylamine. The latter was also measured because it is a major metabolite of phenylalanine and considered to be a neuromodulator.

The plasma amino acids, with the exception of tryptophan, were analyzed by phenylisothiocyanate (PITC) derivation followed by HPLC. The analysis of tryptophan was performed using HPLC with spectrofluormetric detection.

The plasma values of the amino acids were studied both as actual levels and as the ratio of phenylalanine level to the level of the other large neutral amino acids in the plasma. This ratio serves as an index of the entry of phenylalanine into the brain, which accounts for the competition of the other large neutral amino acids (LNAA) with phenylalanine (Phe) at the blood brain barrier, as discussed previously. This ratio is calculated as follows:

$$\text{Phe/LNAA} = \frac{[\text{phenylalanine}]}{(\text{isoleucine} + \text{leucine} + \text{valine} + \text{tyrosine} + \text{tryptophan} + \text{histidine} + \text{threonine})}$$

This study showed that greater than 50% of all 42 patients with TD (including males and females) exhibited either remittance or significant attenuation of symptoms at the two hour post protein challenge point. Moreover, several differences were detected in the plasma values between the 30 male patients whose symptoms were or were not remitted (gender differences in large neutral amino acid metabolism do not allow for mixed sex data analysis and our numbers of females were too small to analyze separately). In particular, those patients whose TD symptoms persisted had significantly higher post challenge phenylalanine to large neutral amino acid ratios.

The change in plasma values from fasting to post challenge also differentiated the TD symptom remission group of patients from the TD symptom persistence group. As seen in Table 1, for these 30 male schizophrenics there were larger percentage changes in the levels of phenylalanine, tyrosine, and valine (valine being one of the branched chain amino acids), in the symptom remission group. In addition, the tryptophan/large neutral amino acid ratios significantly decreased in both groups, and the decrease was 35% greater in the remittance group.

Thus, the most notable differences were:
(a) that the valine/large neutral amino acid ratio increased significantly in the symptom remission group of patients, but not in the persistence group;
(b) the phenylethylamine (PEA) level, which is the major metabolite of phenylalanine, was significantly increased in the symptom persistence group of patients, but not in the remission group; and
(c) the magnitude of the decrease in the tryptophan/LNAA ratio was significantly greater in the symptom remission group than in the persistence group.

The present inventor has two complimentary speculations as to how the BCAA enriched meal served to alleviate or reduce TD symptoms. The first speculation is that because of the significant decrease in the tryptophan/LNAA ratio seen for the TD remission group the TD remission may have been at least partly modulated by the decrease in tryptophan/LNAA and resultant decrease in brain serotonin. This position is supported by the fact that it has been demonstrated in psychiatric patients that brain serotonin content is dependent on plasma tryptophan levels (Delgado, P. L., Charney, D. S., Price, L. H., Aghajanian, G. K., Landis, H., Heninger, G. R., "Serotonin function and the mechanism of antidepressant action. Reversal of antidepressant-induced remission by rapid depletion of plasma tryptophan," Arch. Gen. Psychiatry, 1990, 47:411–418). The present inventor speculates thus that the decrease in brain serotonin effected by the decrease in the tryptophan/LNAA may relieve over stimulation of supersensitive serotonin receptors, which may underlie TD symptomatology. The second speculation is based on the Study Two data which showed that the patients in whom TD persisted had a significant post protein challenge increase in phenylethylamine levels not seen for the TD remission patients. The present inventor speculates that the increase in phenylethylamine acted directly at the serotonin receptor to maintain TD symptom status quo. The pharmacology of phenylethylamine has been extensively studied in animals and that work is helpful to understanding the present inventor's speculation. One aspect of this work has shown that phenylethylamine produces a motor syndrome which can be blocked by serotonin antagonists and prevented by drugs that cause depletion of serotonin. Thus, it has been suggested that phenylethylamine acts directly at serotonin receptors to produce the syndrome (Sloviter, R. S., Connor, J. D., Drust, E. G., "Serotonergic properties of b-phenylethylamine in rats," Neuropharmacology, 1980, 19:1071–1074; Dourish, C. T., "Behavioral effects of acute and chronic b-phenylethylamine administration in the rat: evidence of the involvement of 5-hydroxytryptamine," Neuropharmacology, 1981, 20:1067–1072). The TD persistent patients in Study Two may chronically experience relatively higher levels of phenylethylamine in response to the daily intake of protein. Because they may produce more phenylethylamine, they may therefore be sensitized to this trace amine similarly to the animals in the experiment noted above (Dourish, C. R., "Behavioral effects of acute and chronic b-phenylethylamine administration in the rat: evidence for the involvement of 5-hydroxytryptamine," Neuropharmacology, 1981, 20:1067–1072). If phenylethylamine works directly at a serotonin receptor, excess levels may have overridden any benefit from the decrease of brain tryptophan, contributing to TD persistence.

TABLE 1

Change from Fasting to Postloading
TD Symptom Remission vs TD Symptom Persistence
Mean Values ± SD

| | Fasting | Post-loading | Percent Change** | t*** | p* |
|---|---|---|---|---|---|
| TD Symptom Remission (n = 15) | | | | | |
| Plasma Levels**** | | | | | |
| PEA | 87.5 ± 30.5 | 92.7 ± 21.8 | +5.9 | 0.9 | |
| PHE | 55.5 ± 14.9 | 70.6 ± 16.9 | +27.2 | 3.4 | .0045* |
| TYR | 64.8 ± 17.1 | 84.3 ± 23.5 | +30.1 | 3.3 | .0047* |
| TRP | 61.7 ± 6.9 | 62.3 ± 6.8 | +1.0 | 0.6 | |
| BCAA | 413.9 ± 94.5 | 569.9 ± 143.1 | +37.8 | 3.9 | .0061* |
| Plasma LNAA Ratios | | | | | |
| PHE | 0.076 ± 0.011 | 0.074 ± 0.011 | −2.7 | −0.5 | |
| TYR | 0.090 ± 0.022 | 0.090 ± 0.020 | 0 | −0.1 | |
| TRP | 0.085 ± 0.013 | 0.066 ± 0.010 | −22.4 | −5.7 | .0001* |
| VAL | 0.368 ± 0.055 | 0.388 ± 0.059 | +SA | 2.5 | .0258* |
| TD Symptom Persistence (n = 15) | | | | | |
| Plasma Levels**** | | | | | |
| PEA | 82.9 ± 192 | 95.1 ± 19.2 | +14.7 | 3.1 | .0095* |
| PHE | 58.2 ± 11.5 | 69.1 ± 11.6 | +18.7 | 4.0 | .0014* |
| TYR | 69.3 ± 14.8 | 85.3 ± 22.6 | +23.1 | 3.2 | .0058* |
| TRP | 56.8 ± 8.4 | 5.93 ± 13.0 | +4.4 | 0.9 | |
| DCAA | 377.8 ± 78.4 | 478.5 ± 108.6 | +26.7 | 3.4 | .0047* |
| Plasma LNAA Ratios | | | | | |
| PHE | 0.085 ± 0.010 | 0.094 ± 0.010 | −1.2 | −0.0 | |
| TYR | 0.103 ± 0.012 | 0.103 ± 0.012 | 0 | −0.2 | |
| TRP | 0.084 ± 0.016 | 0.070 ± 0.012 | −16.7 | −3.2 | .0072* |
| VAL | 0.340 ± 0.040 | 0.348 ± 0.040 | +2.4 | 1.4 | |

*Only p values significant according to Holm/Bonferroni procedure listed.
**Postloading/Fasting
***Matched t-test based on changes from Fasting to Postloading (df = 14).
****PEA expressed as pg/ml, amino acids as nmol/ml Overall, including men and women, 21 of 42 patients known to have chronic TD had remission of symptoms when rated two hours after ingesting the protein meal with high BCAA content. An additional 7 patients had symptom decreases of 33% or more. As noted, differences were seen between the males whose symptoms remitted and those for whom they did not in the plasma values data analyses presented.

The results of Study Three lead us to think that the finding of 28 out of 42 patients (67%) experiencing either a remission or decrease in symptoms (Study Two) is a technology-restricted finding and with a change in technology the symptom attenuation would be seen in a higher percentage of patients. In the first place, in Study Two all patients regardless of their weight were given the same size protein meal. In Study Three when we used a weight adjusted dose (100 mg/kg) of phenylalanine, the post challenge metabolic response difference between TD Yes/No groups was much stronger statistically than the difference had been in Study Two. Further in Study Two, the BCAA content had to compete with the 3.6 g of phenylalanine for brain entrance; so that in administering the BCAA alone as a dietary supplement we could expect to improve our rate of symptom improvement.

While the treatment discovery herein is applicable to female patients since an equal percentage of males and females (50%) in Study Two (see above) experienced a symptom remission after the protein challenge, the significant association between plasma indices of phenylalanine and TD was obtained in males only (Study Three, see above). In that study, which unlike in Study Two had a sufficient number of females (n=103) for a separate analysis, a metabolic response to a phenylalanine challenge did not distinguish females with TD from those without the disorder. Thus, the post challenge levels of Phe and Phe/LNAA ratio have discriminated TD in males only (Study Two and Three, see above), but the remission potential of the dietary BCAA was observable in 50% of the female patients, the same proportion as observed in males (Study Two). While the basis for the gender differences observed are at present poorly understood, there is ample evidence that females metabolize amino acids differently from males (Bremer, H. J., Duran, M., Kamerling, J. P., Przyrembel, H. and Wadman, S. D., *Disturbances of Amino Acid metabolism: Clinical Chemistry and Diagnosis*, Baltimore: Urban & Schwarzenberg, 1981; Hagenfeldt, L., Bjerkenstedt, L., Edman, G., Sedvall, G. and Wiesel, F. A., "Amino acids in plasma and CSF and monoamine metabolites in CSG: interrelationship in healthy subjects," *J. Neurochem.*, 42(3):833–837, 1984; Bjerkenstedt, L., Edman, G. Hagenfeldt, L., Sedvall, G. and Wiesel, F. A., "Plasma amino acids in relation to cerebrospinal fluid monoamine metabolites in schizophrenic patients and healthy controls," *Br. J. Psychiatry*, 147:276–282; Rao, J. L., Gross, G., Strebel, B., Braunig, P., Huber, G. and Klosterkotter, J., "Serum amino acids, central monoamines, and hormones in drug-naive, drug-free, and neuroleptic-treated schizophrenic patients and healthy subjects," *Psychiatry Res.*, 34:243–257, 1990). These metabolic differences may in some part be due to influences of the menstrual cycle. There are also several gender-based differences in brain patterns of amino acid derived neurotransmitters, some of which are present during development and at birth, others of which assert themselves as a result of sexual maturation. Therefore, although the plasma levels of phenylalanine at present do not serve as a risk factor for TD in females, with further investigation it might be shown that they do if variability due to gender related factors can be controlled for experimentally. Alternatively, a plasma parameter related to phenylalanine metabolism which is less sensitive to gender differences may be found for females. Alternatively, a modification of the treatment may be made for females if it can be established that the pathophysiology of TD in females is different from that in males. Nevertheless, at present, based on empirical evidence in hand from Study Two, efficacy of the invention is anticipated to be equivalent in both sexes.

EXAMPLE 2

A multi-challenge pilot study (Study Four) with a limited number of patients was carried out in order to understand further the unexpected and therefore uncontrolled finding in Example 1 (Study Two) of the elimination or the reduction of TD symptoms in psychotic patients with a meal rich in BCCA. The multi-challenge study with a tightly controlled design found that 3 out of 4 patients showed TD symptom decreases (ranging from 37%–96%) with BCAA dietary supplement challenges; and 6 out of 6 patients showed symptom decreases (ranging from 46%–99%) when taking the same BCAA-rich protein challenge breakfast of Example 1 (Study Two).

In this study, 8 male patients were enrolled in an attempt to address the following questions:

Study Questions a) Would a meal of different composition have caused a TD symptom remission?

b) Could we replicate the decrease in TD symptoms seen with the Study Two protein challenge meal?

c) Would a dietary supplement of BCAA be an adequate substitute for the Study Two protein challenge meal?

d) Do the BCAA dietary supplement challenges reduce TD symptoms?

e) Do the patients respond to the phenylalanine challenge with an increase in TD symptom severity?

Study Procedure

1. A single patient was exposed over a period of several weeks to multiple dietary challenges, at the rate of one baseline day and one challenge day per week.

2. The baseline days were Tuesdays and the challenge days were Wednesdays.

3. On both Tuesdays and Wednesdays a videotaped evaluation procedure for TD was conducted and videotaped TD movement count sessions were held. These were 2 hours post coffee on Tuesday and 2 hours post challenge on Wednesday. Movement counts were blindly rated from the videotapes by the present inventor.

4. Evaluation sessions were conducted at the same time on both days with patients fasting (except for one cup of decaffeinated coffee) on the baseline days.

Study Challenges

1. The Study Two protein challenge breakfast (the same high BCAA breakfast that produced the TD symptom remission in Example 1).

2. A carbohydrate challenge breakfast; 223 grams of carbohydrates, 1369 calories, less than 4% protein.

3. A 100 mg/kg challenge of Phe.

4. A BCAA dietary supplement as follows:

a) 2 patients had 209 mg/kg doses of BCAA powder given in orange juice b) 1 patient had a 275 mg/kg dose of BCAA powder given in orange juice c) 2 patients had a flavored formulation containing BCAA 150 mg/kg or 275 mg/kg.

The above dosing is in mg/kg patient body weight.

Data that was obtained from this trial on study questions a) Would any meal have caused a TD symptom remission?

The answer to that question is No.

Four patients ate both the Study Two protein challenge breakfast and our carbohydrate challenge meal. Two patients showed an increase in TD symptoms with one meal and a decrease with the other and two patients showed a substantially greater decrease in symptoms with one meal over the other.

1. Patient A showed a 73% decrease in symptoms with the Study A protein challenge breakfast for lateral jaw, choreo/athetoid tongue and lip pursing movements. He showed an 88% increase in the same set of symptoms with the carbohydrate challenge meal.

2. Patient B showed a 46% decrease in symptoms with the Study Two protein challenge breakfast for choreo/athetoid tongue and lip movements. He showed a 95% decrease in the same set of symptoms with the carbohydrate challenge meal. This patient has coexisting TD and tardive dystonia.

3. Patient C showed a 59% decrease in symptoms with the Study Two protein challenge breakfast for choreo/athetoid tongue movements. He showed an 80% decrease in the same symptoms with the carbohydrate challenge meal.

4. Patient D showed a 62% decrease in symptoms with the Study Two protein challenge breakfast for choreo/athetoid tongue movements and tongue protrusions. He showed a 4% increase in those same symptoms with the carbohydrate challenge meal.

b) Could we replicate the decrease in TD symptoms with the Study Two protein challenge meal?

The answer to that question is yes, 100% of the patients who ate the meal experienced a decrease in TD symptoms.

Six patients ate the study breakfast and all 6 or 100% experienced a decrease in TD symptoms ranging from 46% to 99%.

The four patients listed above in answer to Question a) showed decreases in TD symptoms ranging from 46% to 73% two hours after completing the Study Two protein challenge breakfast.

Two other patients who ate the Study A protein challenge breakfast but would not eat the carbohydrate challenge showed the following responses to the Study A protein challenge meal.

5. Patient E showed a 63% decrease in lip movements and a 90% decrease in extremity movements 2 hours after completing the Study Two protein challenge breakfast.

6. Patient F showed a 99% decrease in extremity movements 2 hours after completing the Study Two protein challenge meal.

c) Would a dietary supplement of BCAA be an adequate substitute for the Study Two protein challenge meal:

The answer is yes in 2 out of 3 patients. The one patient for whom the answer is No has coexisting TD and tardive dystonia.

Three patients had both completed a Study Two protein challenge meal and received a BCAA dietary supplement challenge.

1. Patient D showed a 62% decrease in tongue movements with the Study Two protein challenge and a 96% decrease in those movements with the low dose (150 mg/kg) of BCAA in the new formulation.

2. Patient C showed a 59% decrease in tongue movements with the Study Two protein challenge and a 57% decrease in those movements with the BCAA in orange juice challenge of 209 mg/kg.

3. Patient B showed a 25% decrease in tongue and lip movements with the Study Two protein challenge and a 360% increase in those movements with the BCAA in orange juice challenge of 209 mg/kg. This patient has coexisting TD and tardive dystonia.

d) Do the BCAA dietary supplement challenges reduce TD symptoms?

The answer is yes in 3 out of 4 patients. The one patient who did not is our same patient with coexisting TD and tardive dystonia.

Four patients received dietary BCAA supplement challenges. Two of those, Patients D and C as shown just above showed decreases of 96% and 57% with BCAA challenges while Patient B showed a symptom increase.

4. Patient G showed a decrease of 12% in chewing movements with the low dose of the new BCAA formulation (150 mg/kg) and showed a decrease of 37% in those same movements at the high dose (275 mg/kg).

e) Do the patients respond to the phenylalanine challenge with an increase in TD symptom severity?

The answer is Yes for three out of four patients.

Three patients had an increase in TD symptom severity (ranging from 69% to 440%) after the Phe challenge. The fourth patient who did not was again Patient B with coexisting TD and tardive dystonia.

It is known from the inventor's work in a clinic environment that patients with coexisting TD and tardive dystonia have an atypical TD pharmacology in that their TD movements decrease along with their tardive dystonia symptoms when treated with antiparkinson agents for their tardive dystonia. More typically, TD movements increase with increases in antiparkinson agents. It is consistent thus that the one patient with coexisting TD and tardive dystonia had a response pattern in the multi-challenge protocol opposite to that of the other patients.

The BCAA powder given in orange juice and in the flavored formulation at 150 mg/kg and 275 mg/kg consisted of 30 parts—valine, 30 parts-isoleucine and 40 parts-leucine.

Technical aspects of invention

While the invention has been illustrated with administration of a mixture of valine, isoleucine and leucine in nearly equal parts, the benefits of the present invention are realized by administration of at least one of valine, isoleucine and leucine. Further, when a mixture is employed, the ratio of a 2 component and 3 component mixture is in parts by weight 1:100 to 100:1 for a 2-component mixture and for a 3-component mixture, a ratio of by weight of 1:100 to 100:1 for each of the three sub-ratios possible for a 3-component mixture.

The total amount of the branched chain amino acids to be administered, based on molecular weights about those of valine, isoleucine and leucine, is about 50 to 1500 mg/kg of body weight daily, administered in one dose or subdivided into 3 or 4 subdoses spread throughout the day. The branched amino acids can be administered in the form of various pharmaceutical preparations such as tablets, capsules, flavored bars, suspensions, emulsions, etc. Liquid formulations can be prepared by mixing amino acid powder with various liquids such as water and juices such as orange juice, etc. Since the dosage is best optimized for an individual patient, a suggested starting dosage is about 150 to 275 mg/kg per day followed by weekly patient monitoring with increasing or decreasing the dosages in increments of about 50 mg/kg/day as presence or absence, increase or decrease, of symptoms is evaluated, thereby reaching the lowest effective dose.

Also, the present invention contemplates the substitution of synthetic amino acids/compounds of chemical structure differing from that of the naturally occurring amino acids for all or part of the aforementioned naturally occurring amino acids if the synthetic analogs/compounds can be shown by routine experimentation to function in an equivalent manner to the naturally occurring amino acids described herein, but with enhanced efficacy, safety or pharmacokinetics. The synthetic analogs may be characterized by, but are not restricted to, modifications of the structural nucleus of the branched chain amino acids, which have basic formula $NH_2CH(X)COOH$, where X contains a secondary or tertiary carbon atom and contains 3 to 5 carbon atoms, and will be shown to function in a manner analogous (i.e., having similar mechanism of action) of the naturally occurring amino acids.

Although, at this time it is believed that the branched chain amino acids will be useful in most cases of neuroleptic-induced TD, we can see an opposite situation with our patient in Example Two above with the coexisting TD and tardive dystonia. This patient showed a TD symptom worsening with the administration of BCAA and unlike the other patients in the protocol to date, did not show a symptom increase when challenged with phenylalanine. This patient may thus improve if treated with one of the aromatic amino acids, phenylalanine or tyrosine. These reciprocal relationships between movement disorders and their treatment are well known in the field. It is the present inventor's experience in treating patients in the Movement Disorders Clinic she runs for New York State, that it is a common phenomena that anti-Parkinson drugs given to treat neuroleptic induced Parkinsonism in patients with co-existing TD will increase the TD symptom level. The present inventor found unexpectedly that in Study Three outlined above the administration of the challenge does of phenylalanine decreased symptoms of parkinsonism in many patients. Further, in other work that the present inventor has done, she had found that the administration of a dietary product high in BCAA, while it markedly improved TD symptoms, had increased the symptoms of parkinsonism; thus, further supporting the use of aromatic amino acids to treat Parkinsonism. In that same work with the same product it was also found that the symptoms of akathisia had markedly increased as TD improved. It can be expected then given what is known about the competition between the BCAA and the aromatic amino acids for brain entrance that akathisia, a disorder which is most always very troublesome for patients and has proven difficult to treat, might respond to treatment with the aromatic LNAA.

This illustrates the broad applicability of the present invention in treating various abnormal movement disorders by manipulating the amino acids in the blood plasma pool in various ways, for example, at times through the administration of branched chain amino acids and at other times through the administration of aromatic amino acids. The aromatic amino acids will be administered in an amount of about 50 to 1,500 mg/kg of body weight daily, administered in one dose or subdivided into three or four subdoses spread throughout the day.

While the invention has been described in detail, and with reference to specific embodiments thereof, it will be apparent to one of ordinary skill in the art that various changes and modifications can be made therein without departing from the spirit and scope thereof.

What is claimed is:

1. A method of treating tardive dyskinesia, which comprises administering to a patient having tardive dyskinesia at least one amino acid, selected from the group consisting of isoleucine, leucine and valine in an amount sufficient for treating said tardive dyskinesia.

2. The method of claim 1, wherein a mixture of isoleucine, leucine and valine is administered.

3. The method of claim 1, wherein the amino acid is administered in the form of an amino acid enriched meal.

4. The method of claim 1, wherein the amino acid is administered in the form of a dietary supplement.

5. The method of claim 1, wherein the branched chain amino acid is administered in an amount of about 50 mg/kg/day to 1500 mg/kg/day.

6. The method of claim 1, wherein the tardive dyskinesia arises secondary to treatment of the patient with a neuroleptic drug.

* * * * *

UNITED STATES PATENT AND TRADEMARK OFFICE
CERTIFICATE OF CORRECTION

PATENT NO.   : 5,393,784
DATED        : February 28, 1995
INVENTOR(S)  : Mary Ann RICHARDSON It is certified that error(s) appears in the above-identified patent and that said Letters Patent is hereby corrected as shown below:

Column 9, line 68, change "1983" to --1984--.

Column 12, line 33, change "+SA" to --+5.4--;

line 40, change "DCAA" to --BCAA--.

Column 17, line 29, change "does" to --dose--.

Signed and Sealed this

Twentieth Day of February, 1996

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,393,784
DATED : February 28, 1995
INVENTOR(S) : Mary Ann RICHARDSON It is certified that error appears in the above-indentified patent and that said Letters Patent is hereby corrected as shown below:

Columns 11 and 12, Table 1, the first line after "Plasma Levels****", change "82.9 ± 192" to --82.9 ± 19.8--.

Signed and Sealed this

Eleventh Day of June, 1996

Attest:

BRUCE LEHMAN

*Attesting Officer*   *Commissioner of Patents and Trademarks*